(12) United States Patent
Dudar

(10) Patent No.: US 10,758,879 B2
(45) Date of Patent: *Sep. 1, 2020

(54) APPARATUS AND SYSTEM FOR IMPROVED SET-UP OF MULTI-INGREDIENT COMPOUNDER

(71) Applicant: Baxter Corporation Englewood, Englewood, CO (US)

(72) Inventor: Thomas Edward Dudar, Palatine, IL (US)

(73) Assignee: BAXTER CORPORATION ENGLEWOOD, Englewood, CO (US)

( * ) Notice: Subject to any disclaimer, the term of this patent is extended or adjusted under 35 U.S.C. 154(b) by 40 days.

This patent is subject to a terminal disclaimer.

(21) Appl. No.: 16/169,600

(22) Filed: Oct. 24, 2018

(65) Prior Publication Data
US 2019/0054436 A1 Feb. 21, 2019

Related U.S. Application Data

(63) Continuation of application No. 15/386,968, filed on Dec. 21, 2016, now Pat. No. 10,124,308.
(Continued)

(51) Int. Cl.
*B01F 15/02* (2006.01)
*B01F 13/10* (2006.01)
(Continued)

(52) U.S. Cl.
CPC .......... *B01F 15/026* (2013.01); *A61M 39/00* (2013.01); *A61M 39/105* (2013.01);
(Continued)

(58) Field of Classification Search
CPC ... A61M 39/105; A61M 39/00; B01F 15/026; B01F 15/00253; B01F 13/1055;
(Continued)

(56) References Cited

U.S. PATENT DOCUMENTS 3,287,031 A 11/1966 Simmons et al.
3,331,392 A 7/1967 Davidson et al.
(Continued)

OTHER PUBLICATIONS

Baxter, ExactaMix Compounding Systems for Specialty Pharmacies, ExactaMix Brochure, Oct. 16, 2012.
Baxter, ExactaMix 1200 Compounder, Operator Manual, Jan. 2015, Baxter Healthcare Corporation, Englewood Colorado.
Baxter, ExactaMix 2400 Compounder, Operator Manual, Jan. 2015, Baxter Healthcare Corporation, Englewood, Colorado.
(Continued)

*Primary Examiner* — Umashankar Venkatesan
(74) *Attorney, Agent, or Firm* — K&L Gates LLP

(57) ABSTRACT

Apparatus and systems are disclosed for improved set-up of multi-ingredient compounders. An improved apparatus includes a manifold and a plurality of valve members disposed for movement relative to different corresponding ones of a plurality of inlet ports of the manifold. The valve members are moveable to open and close a corresponding fluid passageway between the corresponding inlet port and an internal passageway of the manifold. A plurality of caps are locatable on different corresponding ones of the inlet ports, with each of the caps being engageable with the corresponding valve member for co-movement from a locked position at which the cap is restricted from removal to an unlocked position at which the cap is removable, e.g. by manual, axial retraction of the cap. An improved system includes a compounder controller operable to control valve actuators of the compounder so as to sequentially move the valve members and corresponding caps from locked to unlocked positions in a predetermined sequence, thereby reducing the potential for undesired cross-connections.

19 Claims, 9 Drawing Sheets

Related U.S. Application Data

(60) Provisional application No. 62/273,707, filed on Dec. 31, 2015.

(51) Int. Cl.
*B01F 15/00* (2006.01)
*A61M 39/00* (2006.01)
*A61M 39/10* (2006.01)

(52) U.S. Cl.
CPC .... *B01F 13/1055* (2013.01); *B01F 15/00253* (2013.01); *B01F 2215/0034* (2013.01); *Y10T 137/8766* (2015.04); *Y10T 137/87684* (2015.04)

(58) Field of Classification Search
CPC ..... B01F 2215/0034; Y10T 137/87249; Y10T 137/8766; Y10T 137/87684
See application file for complete search history.

(56) References Cited

U.S. PATENT DOCUMENTS

| | | |
|---|---|---|
| 3,561,505 A | 2/1971 | Ryder |
| 4,789,014 A | 12/1988 | DiGianfilippo et al. |
| 4,804,208 A | 2/1989 | Dye |
| 4,944,424 A | 7/1990 | Wood, Jr. |
| 5,190,525 A | 3/1993 | Oswald et al. |
| 5,865,474 A | 2/1999 | Takahashi |
| 7,490,620 B2 | 2/2009 | Tesluk et al. |
| 2001/0040123 A1 | 11/2001 | Beckham |
| 2016/0045876 A1 | 2/2016 | Kaucky et al. |
| 2016/0310362 A1 | 10/2016 | Lane et al. |
| 2016/0310363 A1 | 10/2016 | Konrad, Jr. et al. |

OTHER PUBLICATIONS

Baxter, Sterile ExactaMix 1200 Valve Set, Instructions for Use, Jul. 2015, Baxter Healthcare Corporation, Englewood, Colorado.
Baxter, Sterile ExactaMix 2400 Valve Set, Instructions of Use, Jul. 2015, Baxter Healthcare Corporation, Englewood, Colorado.

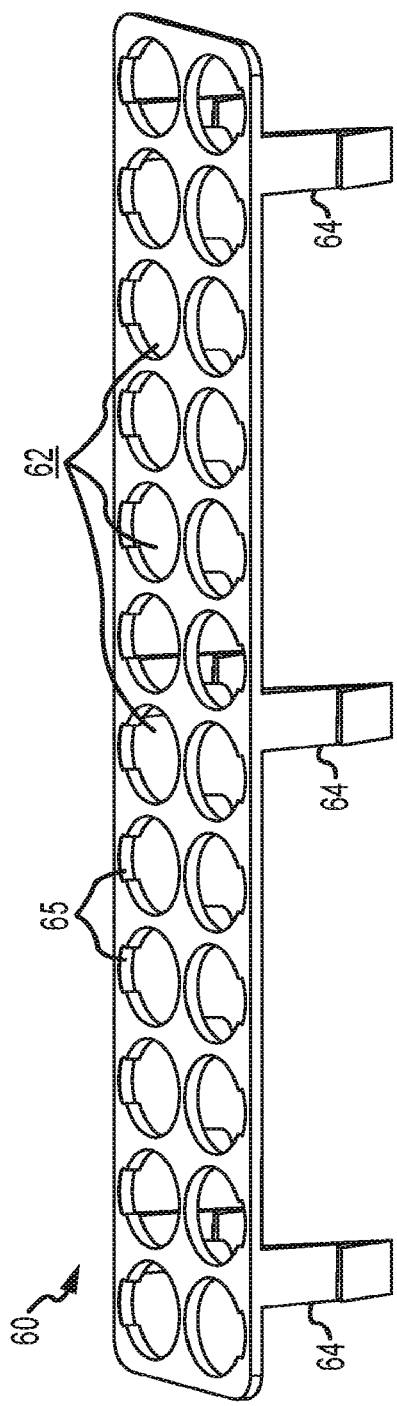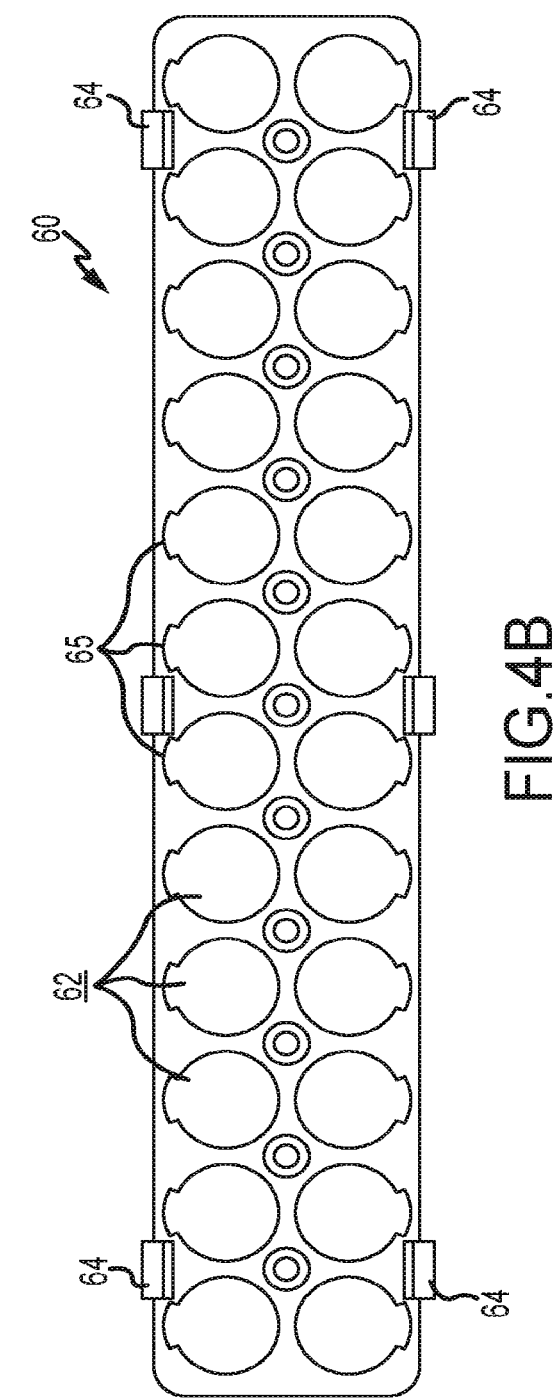
FIG.4A
FIG.4B

APPARATUS AND SYSTEM FOR IMPROVED SET-UP OF MULTI-INGREDIENT COMPOUNDER

RELATED APPLICATIONS

This application is a continuation of U.S. patent application Ser. No. 15/386,968, entitled "APPARATUS & SYSTEM FOR IMPROVED SET-UP OF MULTI-INGREDIENT COMPOUNDER," filed Dec. 21, 2016, which claims benefit of priority to U.S. Provisional Patent Application No. 62/273,707, entitled "APPARATUS AND SYSTEM FOR IMPROVED SET-UP OF MULTI-INGREDIENT COMPOUNDER", filed Dec. 31, 2015, which are incorporated herein by reference in their entirety.

BACKGROUND

Multi-ingredient compounders are utilized to compound desired amounts of different fluid ingredients contained in different source containers into a common receiving receptacle. Typically, the source containers are interconnected to inlet ports of a disposable apparatus interconnected to the compounder and through which the fluid ingredients are flowed to the common receiving receptacle. Such multi-ingredient compounders and disposable apparatus may be utilized to compound fluid ingredients into therapeutic formulations intended for intravenous administration to a patient.

As may be appreciated, tight control is necessary in order to obtain the desired amounts, compounding sequence, and flow parameters for the various ingredients compounded in a given formulation. To date, while high-accuracy compounding is achievable, there remain instances in which compounding personnel inadvertently set up a compounder to compound ingredients in an unintended manner.

By way of primary example, set-up errors may result from interconnecting a tubing set associated with a given fluid ingredient to an inlet port of a disposable apparatus that is intended for interconnection with a different tubing set associated with a different fluid ingredient. Such "cross-connection" errors, if not identified and properly addressed, can result in errors in the relative amounts, compounding sequence and/or flow parameters of the ingredients compounded in a given formulation.

SUMMARY

Apparatus and systems are disclosed herein to provide for improved set-up of multi-ingredient compounders by reducing the risk of cross-connection errors by compounding personnel. In that regard, for purposes of this disclosure the term "set-up" refers to the procedure of interconnecting different predetermined inlet ports of a disposable apparatus, interconnected to a multi-ingredient compounder, to different predetermined tubing sets that are interconnected or interconnectable to different predetermined source containers containing different fluid ingredients to be used in the compounding of one or more given formulation.

In one embodiment a disposable apparatus for use with a multi-ingredient compounder is disclosed that includes a manifold having an internal passageway, an outlet port located at one end of the internal passageway, and plurality of inlet ports to the internal passageway. The embodiment further includes a plurality of valve members, each disposed for movement relative to a different corresponding one of the plurality of inlet ports to open and close a corresponding fluid passageway between the corresponding inlet port and the internal passageway of the manifold. Further, the embodiment includes a plurality of caps, each locatable on a different corresponding one of the plurality of inlet ports and engageable with the corresponding valve member, wherein each of the plurality of caps is (i) restricted from removal from the corresponding inlet port in a locked position when the corresponding valve member is located in a corresponding first predetermined position relative to the corresponding inlet port, and (ii) removable from the corresponding inlet port in an unlocked position when the corresponding valve member is moved to a corresponding second predetermined position relative to the corresponding inlet port.

As will be appreciated, the provision of caps that are positionable in locked and unlocked positions facilitates a reduction in cross-connection errors during compounding set-up by medical personnel.

In contemplated embodiments, each of said plurality of caps is engageable with the corresponding valve member for co-movement therewith, from the locked position to the unlocked position, when the corresponding valve member is moved from the corresponding first predetermined position to the corresponding second predetermined position. In that regard, and as described further below, a controller of a multi-ingredient compounder may be operable during set-up to control movement of the valve members from the corresponding first predetermined positions to the corresponding second predetermined positions, and associated positioning of the corresponding caps from locked to unlocked positions, in a predetermined interconnection sequence that corresponds with the interconnection of a plurality of predetermined source fluid containers to be used with given formulations that are to be compounded.

In some embodiments, each of the valve members may be disposed for rotatable movement between the corresponding predetermined first position and the corresponding predetermined second position, wherein the corresponding cap is co-rotatable from the locked position to the unlocked position. For such purposes, each of the plurality of caps may be slidably disposed on the corresponding inlet port for rotation on and relative to the inlet port during movement from the locked position to the unlocked position, and for removal from the corresponding inlet port in the unlocked position, i.e. by axial retraction of the cap relative to the corresponding inlet port. Further, each of the valve members may comprise a drive member and each of the caps may comprise a complimentary mating member for abutting engagement with and driven rotational movement by the drive member of the corresponding valve member, wherein each of the caps may be slidably disengageable in the unlocked position from the corresponding valve member by axial retraction of the cap.

In some arrangements, the complimentary drive and mating members may comprise one or more of a plurality of complimentarily configured rib(s) and groove(s) each oriented parallel to a center axis of the corresponding cap. Further in that regard, each of corresponding ones of the inlet ports, valve members and caps may be provided to have a common center axis or parallel corresponding center axes.

In some implementations, each of the caps may include at least one locking element. In turn, the manifold may further comprise a plurality of apertures disposed in axially aligned relation to the caps, wherein each of the plurality of caps extends through a different corresponding one of the plurality of apertures when located on the corresponding inlet port. The plurality of apertures may be configured so that the manifold restricts axial movement of the locking element of the corresponding cap when located on the corresponding inlet port in the locked position with the corresponding valve member located in the corresponding first predetermined position relative to the corresponding inlet port.

In some arrangements, the at least one locking element of each of the plurality of caps may comprise at least one peripheral protrusion. In some arrangements, each of the plurality of caps may comprise at least two peripheral protrusions offset about the periphery of the cap. Each of the plurality of apertures may include at least one edge recess configured so that the manifold permits axial passage of the at least one peripheral protrusion of the corresponding cap through the at least one edge recess when the cap is located in the unlocked position with the corresponding valve member located in the corresponding second predetermined position relative to the corresponding inlet port.

In some embodiments, the manifold may include a base portion that defines the internal passageway, the outlet port and the plurality of inlet ports. Further, the manifold may include a locking plate that defines the plurality of apertures, wherein the locking plate may be selectively interconnected to the base portion. As may be appreciated, the locking plate and base portion of the manifold may be disposed in face-to-face relation so that the at least one locking element of each of the plurality of caps is located between the base portion and the locking plate when the corresponding cap is located in the locked position with the corresponding valve member located in the corresponding first predetermined position.

In one approach, the plurality of caps may be located on the plurality of inlet ports (e.g. in locked positions with the corresponding valve members in corresponding first predetermined positions), followed by interconnection of the locking plate to the base portion. Alternatively, the locking plate may be interconnected to the base portion, followed by positioning of the caps on the corresponding inlet ports with the corresponding valve members positioned in the corresponding second predetermined positions.

In some implementations, each of the plurality of caps may include a top end portion having an asymmetric configuration, thereby facilitating user observation/differentiation of a given cap rotated from the locked position to the unlocked position. In that regard, the top end portion of each cap may include two opposing side surfaces and two end surfaces, wherein the side surfaces are wider than the end surfaces. In turn, the side surfaces of each cap may be substantially planar to facilitate manual grasping, e.g. for cap removal from a corresponding inlet port.

In contemplated arrangements, each of the plurality of valve members may close the corresponding fluid passageway between the corresponding inlet port and internal passageway of the manifold when located in the corresponding first predetermined position and the corresponding second predetermined position. Further, each of the plurality of valve members may be disposed for rotatable movement to a third position relative to the corresponding inlet port to open the corresponding fluid passageway between the corresponding inlet port and the internal passageway of the manifold.

In another embodiment, a system for use with a multi-ingredient compounder is disclosed that includes a multi-ingredient compounder having a plurality of valve actuators and a controller for controlling movement of each of the valve actuators. Further, the system includes a disposable apparatus that comprises a manifold having a plurality of inlet ports and a plurality of valve members that are each locatable to interface with a different corresponding one of the plurality of valve actuators of the multi-ingredient compounder for driven movement thereby between a plurality of different positions relative to a different corresponding one of the inlet ports during compounding set-up. The apparatus may comprise a plurality of caps located on different corresponding ones of the inlet ports, wherein the controller of the compounder is operable to separately control movement of each of the valve actuators so as to separately move each of the valve members between at least a corresponding first predetermined position at which the corresponding cap is restricted from removal from the corresponding inlet port, i.e. a locked position, and a corresponding second predetermined position at which the corresponding cap is removable from the corresponding inlet port, i.e. an unlocked position, during compounding set-up procedures.

In contemplated embodiments, each of said plurality of caps is engageable with the corresponding valve member for co-movement therewith, from the locked position to the unlocked position, when the corresponding valve member is moved from the corresponding first predetermined position to the corresponding second predetermined position.

In some arrangements, each of the valve members may be disposed for rotatable movement between the corresponding predetermined first position and the corresponding predetermined second position, wherein the corresponding cap is co-rotatable from the locked position to the unlocked position. For such purposes, each of the plurality of caps may be slidably disposed on the corresponding inlet port for rotation on and relative to the inlet port during movement from the locked position to the unlocked position, and for removal from the corresponding inlet port in the unlocked position by axial retraction of the cap relative to the corresponding inlet port. Further, each of the caps may be slidably disengageable in the unlocked position from the corresponding valve member by such axial retraction of the cap.

In contemplated implementations, the controller may be operable during set-up to individually control movement of the plurality of valve actuators, and correspondingly position each of the plurality of valve members separately from the corresponding first predetermined position to the corresponding second predetermined position, in a predetermined interconnection sequence. In turn, the corresponding caps may be separately positioned from the locked position to the unlocked position in accordance with the predetermined interconnection sequence. In that regard, predetermined ones of the plurality of inlet ports may be successively provided for access, i.e. by removal of the corresponding cap when located in the unlocked position, for interconnection to different predetermined ones of a plurality of tubing sets in accordance with the predetermined interconnection sequence, wherein the tubing sets are interconnected or interconnectable to different predetermined ones of a plurality of source containers containing different ingredients to be compounded in one or more of given formulations.

In some arrangements, the controller may be operable to require, between and for completion of successive steps in the predetermined interconnection sequence, the receipt and validation by the controller of an input indicative of a desired interconnection between a corresponding predetermined one of the plurality of inlet ports and a corresponding predetermined one of the plurality of source containers utilizing a corresponding predetermined tubing set. In some arrangements, the required input may comprise digital identifying data read from one or more machine readable marking(s) (e.g. a machine readable marking located on the corresponding predetermined source containers and/or on the corresponding predetermined tubing set). In turn, the controller may be operable to compare the digital identifying data to stored data corresponding with the predetermined source container and/or the predetermined tubing set, and thereby validate the establishment of the desired interconnections (i.e. in accordance with predetermined interconnection sequence). The stored data may comprise data that corresponds with a predetermined plurality of source containers to be interconnected and available for use in compounding one or a plurality of predetermined formulations.

In another arrangement, after interconnection of each of the plurality of inlet ports with a different predetermined one of the plurality of source containers, utilizing a different predetermined one of the plurality of the tubing sets, in accordance with the predetermined interconnection sequence, the controller may be operable to require an input in relation to each of the plurality of inlet ports, wherein the input is indicative of a desired interconnection between the given inlet port and a corresponding predetermined one of the plurality of source containers utilizing a corresponding predetermined tubing set. In some arrangements, the required input may comprise digital identifying data read from one or more machine readable marking(s) (e.g. a machine readable marking located on the corresponding predetermined source containers and/or on the corresponding predetermined tubing set). In turn, the controller may be operable to compare the digital identifying data to stored data corresponding with the predetermined source container and/or the predetermined tubing set, and thereby validate the establishment of the desired interconnections.

In some embodiments, after interconnection (e.g. validated interconnection) of each of the plurality of inlet ports with the corresponding predetermined source container, utilizing the corresponding predetermined tubing set, the controller may be operable to successively move each valve actuator and thereby successively position each corresponding valve member, in accordance with a predetermined priming sequence, to a corresponding predetermined third position to open the corresponding fluid passageway for flowing the corresponding fluid ingredient from the predetermined source container and through the corresponding tubing set, inlet port and fluid passageway, so as to prime the tubing sets and the disposable apparatus. In some embodiments, between successive steps of the predetermined priming sequence, after positioning each valve member to the corresponding predetermined third position and priming of the corresponding tubing set, inlet port and fluid passageway, the controller may be operable to control the corresponding valve actuator to move the corresponding valve member to another predetermined position relative to the corresponding inlet port (e.g. to the corresponding first predetermined position) so as to close the corresponding fluid passageway. Upon completion of the predetermined priming sequence a given set-up procedure may be considered complete, wherein the compounder and disposable apparatus are configured for subsequent compounding of one or a plurality of predetermined formulations.

As may be appreciated, the disposable apparatus of the system embodiment may include additional features of disposable apparatus embodiments otherwise disclosed herein. For example, each of the plurality of caps may comprise an asymmetric top end portion (e.g. having side surfaces that are wider than end surfaces thereof). In turn, the disposable apparatus may be provided for set-up so that each of the plurality of caps is initially located on the corresponding inlet port in the locked position and in a common first orientation (e.g. so that side surfaces of each cap are oriented parallel to a center axis of the manifold). As such, upon subsequent rotation of a given cap to the unlocked position during set-up, the cap will assume a second orientation (e.g. so that side surfaces of the cap are oriented transverse to the center axis of the manifold), thereby facilitating ready user observation/differentiation of the unlocked cap.

Additional features and advantages of the present invention will become apparent upon consideration of the further description that follows.

BRIEF DESCRIPTION OF THE DRAWINGS

FIG. 4A is a perspective front view of a locking plate embodiment comprising disposable apparatus embodiment shown in FIGS. 2A-2C.

FIG. 4B is a top view of the locking plate embodiment shown in FIG. 4A.

DETAILED DESCRIPTION

The following description is not intended to limit the invention to the forms disclosed herein. Consequently, variations and modifications commensurate with the following teachings, skill and knowledge of the relevant art, are within the scope of the present invention. The embodiments described herein are further intended to explain modes known of practicing the invention and to enable others skilled in the art to utilize the invention in such, or other embodiments and with various modifications required by the particular application(s) or use(s) of the present invention.

Figure 1A:
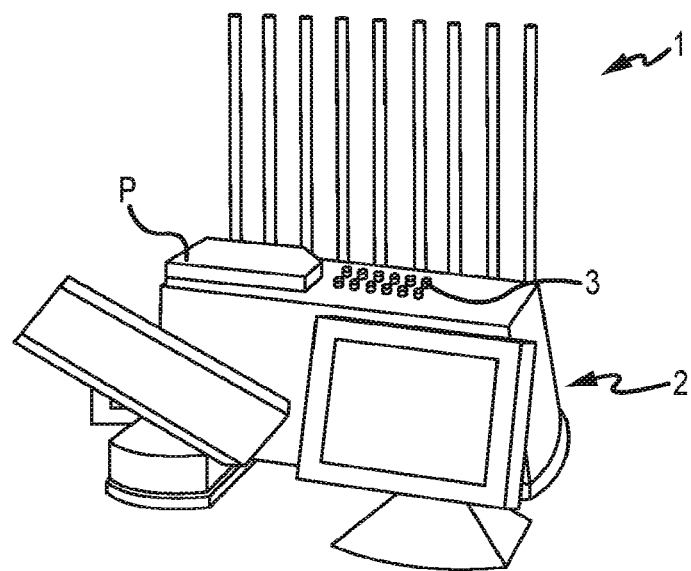
FIG. 1A is a perspective view of a multi-ingredient compounder of a system embodiment.
Figure 1B:
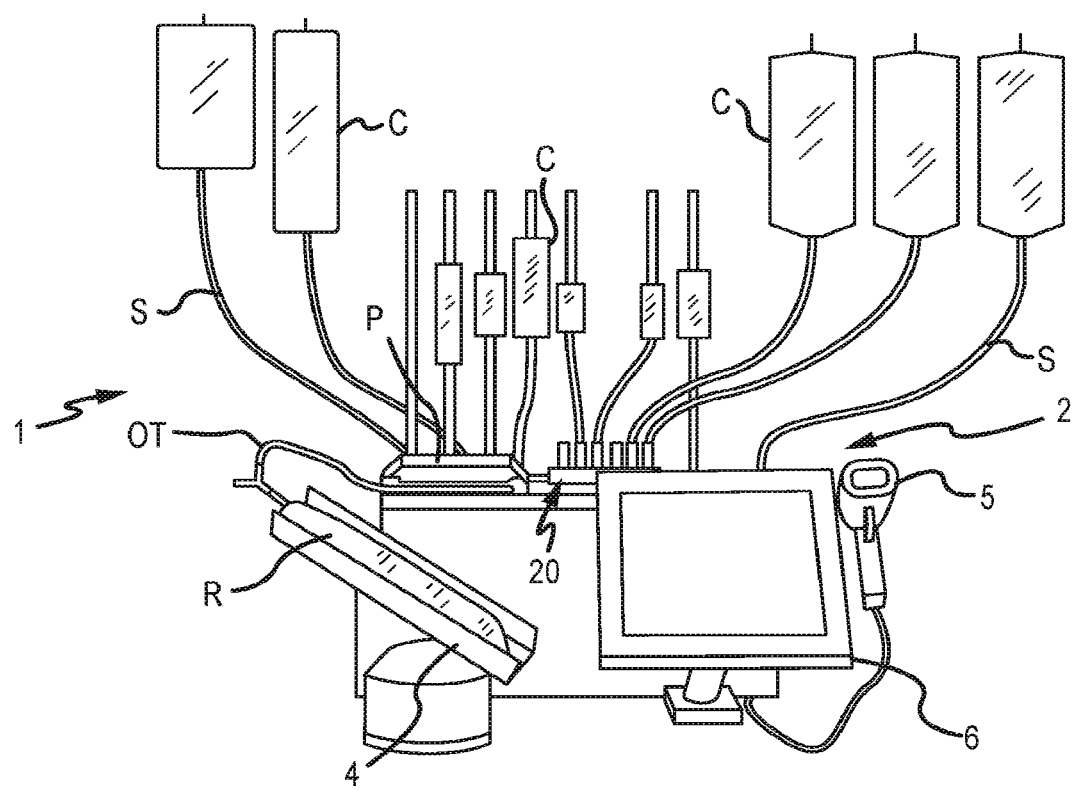
FIG. 1B is a perspective view of a disposable apparatus interconnected to the multi-ingredient compounder of a system embodiment.

One embodiment of a system (1) is generally shown in FIGS. 1A and 1B, and includes a multi-ingredient compounder (2) having a plurality of valve actuators (3). The compounder (2) may further include an internal controller for controlling rotational movement of the valve actuators (3), including control during compounding set-up as described herein. By way of example, the controller may comprise one or more computer processor(s) configurable by execution of preprogrammed instructions comprising one or more software modules and utilizing one or more associated databases stored at compounder (2) (e.g. stored in non-transitory memory) to control the rotational movement of the plurality of valve actuators (3).

In turn, and as shown in FIG. 1B, a disposable apparatus (20) having a plurality of valve members (not shown in FIG. 1B) may be located to interface with the valve actuators (3), wherein the controller of compounder (2) is operable to selectively control the sequential flow of fluid ingredients from source containers C through the disposable apparatus (20) and into a receiving receptacle R. In that regard, tubing sets S may be fluidly interconnected to the source containers C (e.g. via a spike port provided at the first end of each tubing set), and fluidly interconnected to the disposable apparatus (20) (e.g. via a cylindrical push on/pull off end port provided at a second end of each tubing set). As illustrated, the source containers C may be suspended for gravity fluid flow. An outlet port of the disposable apparatus (20) may be interconnected to an outlet tubing OT that is locatable in a pump P (e.g. a peristaltic pump). In turn, the pump P may be controlled by the controller of the compounder (2) for metered fluid flow through the outlet tubing OT so that a predetermined amount of the fluid ingredients in source containers C may be selectively flowed through the disposable apparatus (20), outlet tubing OT, and into the receiving receptacle R.

As shown in FIGS. 1A and 1B, a gravimetric device (4) may be provided to support the receiving receptacle R and provide a gravimetric output indicative of a weight of the receiving receptacle R to the controller of the compounder (2) for use in verifying the amount of fluid ingredients flowed in to the receiving receptacle R during compounding. Further, as shown in FIG. 1B, a reader device (5) may be provided to read one or more machine-readable markings provided on or in association with, and comprising identifying data for, each of the tubing sets S and/or source containers C, and to provide a corresponding output indicative of the identifying data. In turn, such output may be provided to the controller of the compounder for use during set-up to verify an intended interconnection of a desired source container C to a desired tubing set S, and/or an intended interconnection of a desired tubing set S to a given intended one of a plurality of inlet ports of the disposable apparatus (20). Further, a user interface (6) may be provided at the compounder (2) to facilitate interactive data input and data output at the compounder (2).

Figure 2A:
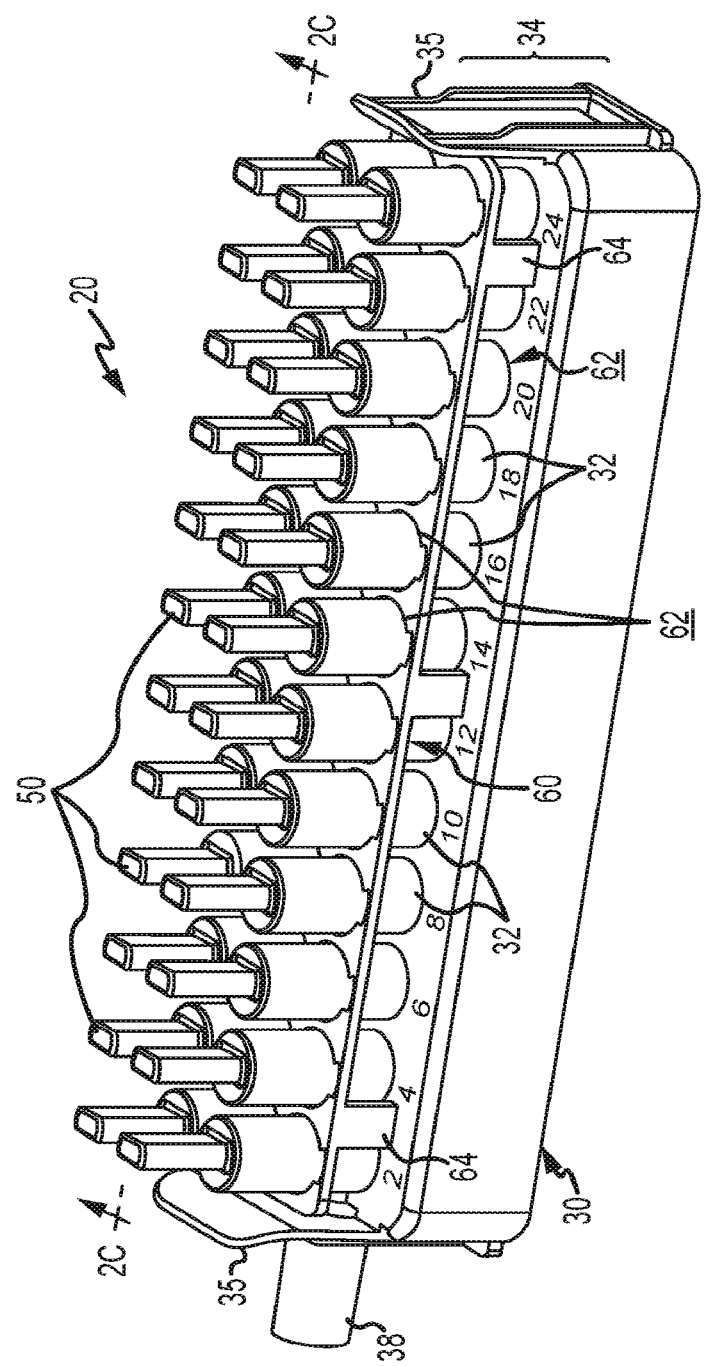
FIG. 2A is a perspective view of a disposable apparatus embodiment employable in the system embodiment of FIGS. 1A and 1B.
Figure 2B:
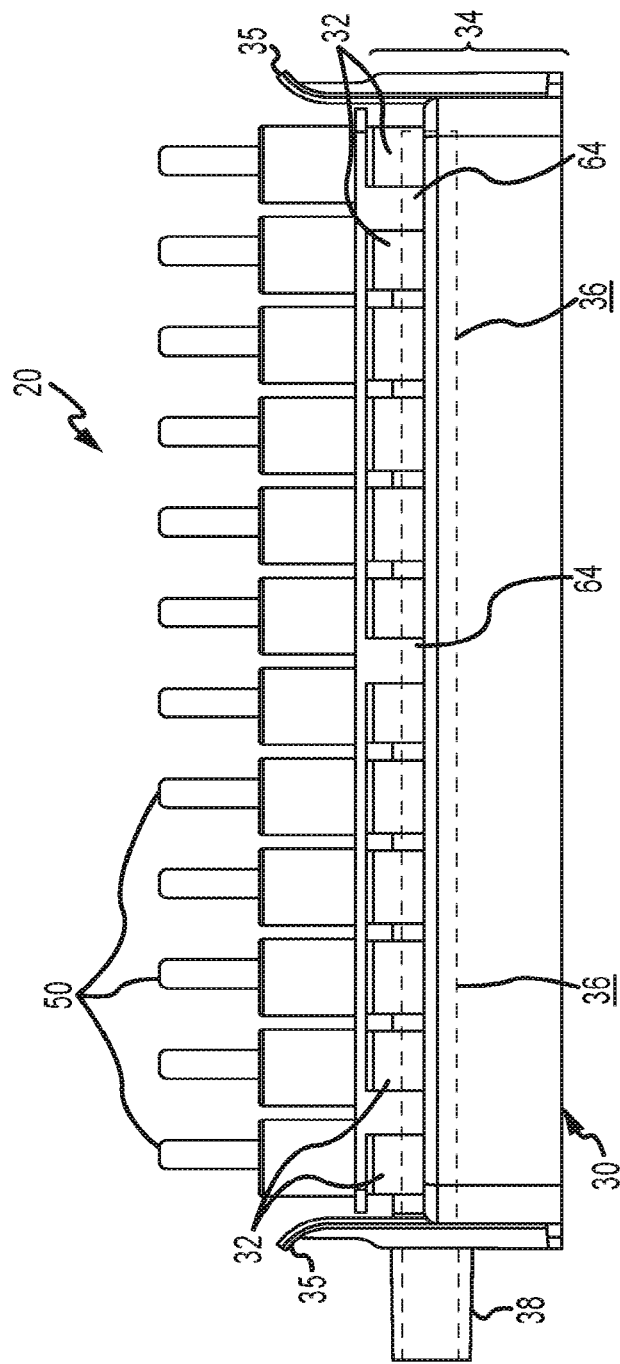
FIG. 2B is a side view of the disposable apparatus embodiment shown in FIG. 2A.
Figure 2C:
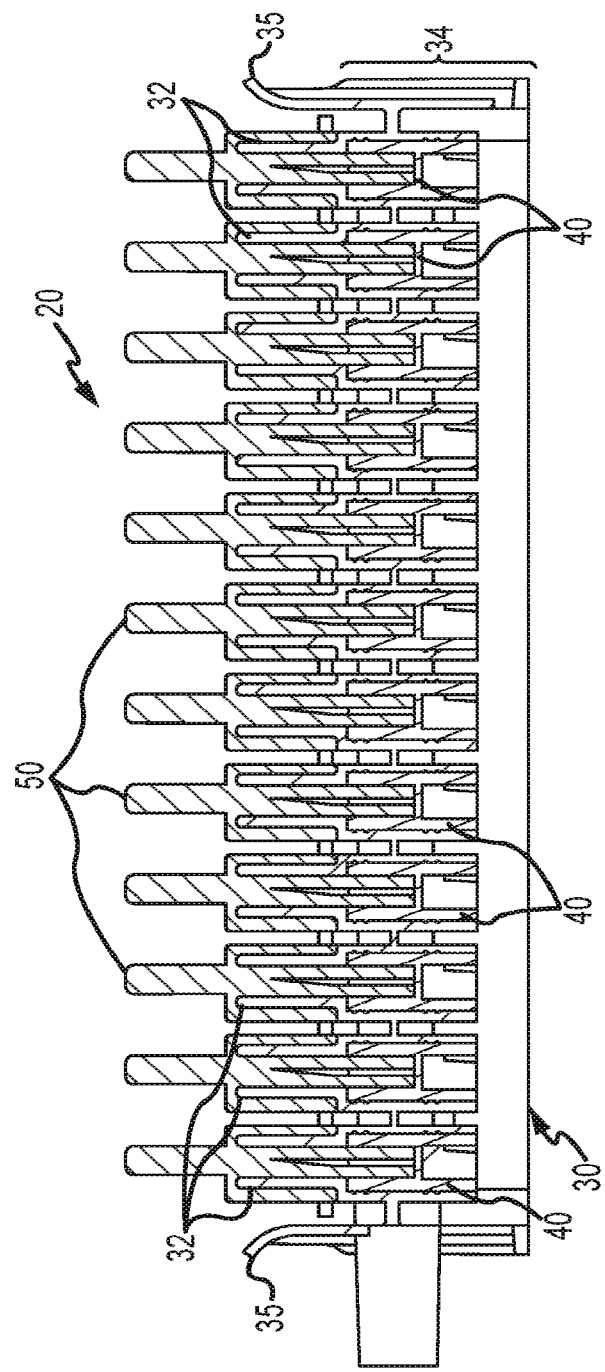
FIG. 2C is a side cross-sectional view of the disposable apparatus embodiment shown in FIGS. 2A and 2B, as viewed at cross-sectional plane 2C shown in FIG. 2A.

Reference is now made to FIGS. 2A, 2B and 2C which illustrate one embodiment of a disposable apparatus (20). The disposable apparatus (20) may include a manifold (30) having a plurality of inlet ports (32). Each of the inlet ports (32) may be fluidly interconnectable by a corresponding different fluid passageway to an internal passageway (36) of the manifold (30), shown in phantom lines in FIG. 2B. In turn, the internal passageway (36) may extend to an outlet port (38) of the manifold (30). In the illustrated embodiment, a base portion (34) of the manifold (30) may include the inlet ports (32), internal passageway (36) and outlet port (38). The base portion (34) may include end clips (35) for selective interconnection to and disconnection from the compounder (2) described above in relation to FIGS. 1A and 1B.

Further, a plurality of caps (50) may be located on the inlet ports (32) of the manifold (30), wherein each cap (50) is restricted from removal from the corresponding inlet port (32) in a locked position and removable from the corresponding inlet port (32) in an unlocked position. As best shown in FIGS. 2A and 2B, the manifold (30) may further include a locking plate (60) having a plurality of apertures (62), wherein each cap (50) extends through a different one of the apertures (62) of locking plate (60). The locking plate (60) may be provided with a plurality of downward extending support members (64) configured for snap-fit engagement within openings provided on a top surface of the base portion (34) of the manifold (30), wherein the locking plate (60) may be supported by and spaced from the top surface of the base portion (34) with each of the apertures (62) axially aligned with a different one of the inlet ports (32) and caps (50) located thereupon.

As shown in FIG. 2C, the disposable apparatus (20) may further include a plurality of valve members (40) each disposed for rotatable movement relative to a different corresponding one of the plurality of inlet ports (32). In that regard, each of the valve members may be rotated to open and close the corresponding fluid passageway between the corresponding inlet port (32) and the internal passageway (36) of the manifold (30).

More particularly, and as shown in FIG. 2C, each of the inlet ports (32) may comprise an upper tubular portion and a stepped-out, lower tubular portion fluidly adjoined thereto, and each of the valve members (40) may include a tubular top end portion rotatably and slidably disposed in the lower tubular portion of the corresponding inlet port (32). Further, a sidewall of the lower tubular portion of each inlet port (32) may include an inlet opening (not shown in FIG. 2C) to the internal passageway (36) of the manifold (30). In turn, and as further described below, a sidewall of the tubular top end portion of each of the valve members (40) may include a hole therethrough, wherein the valve member (40) may be rotatably positioned in a plurality of positions in which the hole is blocked (e.g. by the sidewall of the lower tubular portion of the corresponding inlet port (32)), and wherein the valve (40) may be rotatably positioned to align the hole thereof with the inlet opening of the corresponding inlet port (32) to open the corresponding fluid passageway to the internal passageway (36) of the manifold (30).

As illustrated in FIG. 2C, each of the caps (50) may be provided for engagement with a different corresponding one of the valve members (40) at the corresponding inlet port (32) for co-rotation therewith, including in particular, co-rotation from the locked position to the unlocked position when the corresponding valve member (40) is rotated from a corresponding first predetermined position to a corresponding second predetermined position. In that regard, and as further described below, each of the valve members (40) may comprise a drive member and each of the caps (50) may comprise a complimentary mating member for abutting engagement with and driven rotational movement by the drive member of the corresponding valve member (40), wherein the drive and complimentary mating members are configured so that each of the caps (50) is slidably disengageable in the unlocked position from the corresponding valve member (40), e.g. upon axial retraction of the cap from the corresponding inlet port.

In some arrangements, the complimentary drive and mating members may comprise one or more of a plurality of complimentarily configured rib(s) and groove(s) each oriented parallel to a center axis of the corresponding cap (50). Further in that regard, each of corresponding ones of the inlet ports (32), valve members (40) and caps (50) may be provided to have a common center axis or parallel corresponding center axes.

As may be appreciated, each of the caps (50) may be slidably disposed on the corresponding inlet port (32) for rotation on and relative to the inlet port (32) during rotational movement from the locked position to the unlocked position, and for removal from the corresponding inlet port (32) in the unlocked position by axial retraction of the cap (50) relative to the corresponding inlet port (32).

Figure 3A:
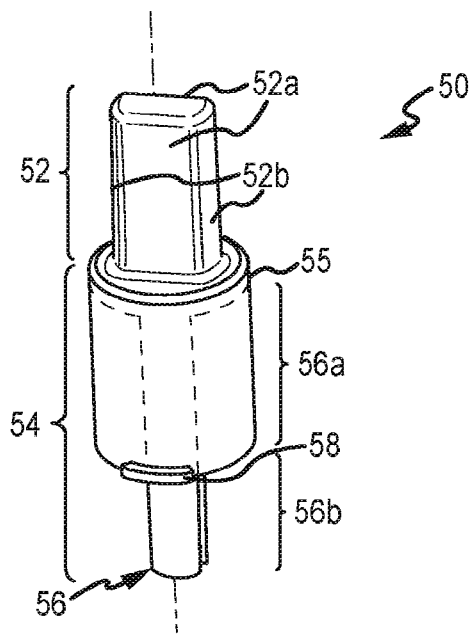
FIG. 3A is a perspective view of an embodiment of a cap comprising the disposable apparatus embodiment shown in FIGS. 2A-2C.
Figure 3B:
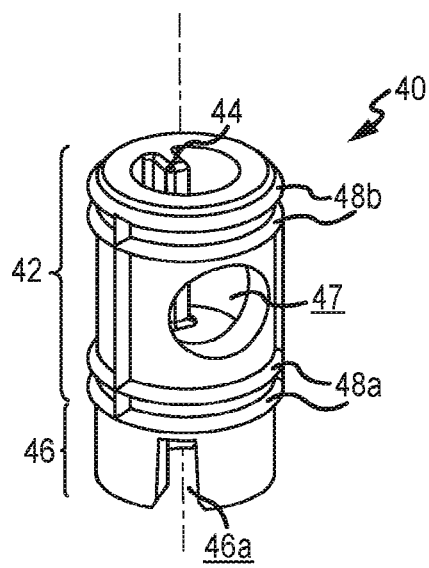
FIG. 3B is a perspective view of an embodiment of a valve member comprising disposable apparatus embodiment shown in FIG. 2C.

Reference is now made to FIGS. 3A and 3B which illustrate one embodiment of a cap (50) and corresponding valve member (40). The cap (50) may include a top end portion (52), and a manifold engagement portion (54) interconnected to the top end portion.

The top end portion (52) may have an asymmetric configuration to facilitate user observation and differentiation of a given cap rotated from the locked position to the unlocked position. Further, the top end portion (52) may be configured to facilitate manual grasping and manipulation by a user. For example, the top end portion (52) may include two opposing side surfaces (52*a*) and two end surfaces (52*b*), wherein the side surfaces (52*a*) are considerably wider than the end surfaces (52*b*). Further, the opposing side surfaces (52*a*) may be of a substantially planar configuration. In some arrangements, the opposing side surfaces (52*a*) may be textured to further facilitate grasping by a user. Additionally, in some arrangements, the opposing side surfaces (52*a*) may be patterned or colored in manner to further facilitate visual differentiation by a user.

As shown in FIG. 3A, the manifold engagement portion (54) may include an inverted, cup-shaped housing (55) and a post-shaped engagement member (56) having a first end portion (56*a*) interconnected to an internal ceiling of the cup-shaped housing (55) of the caps (50) and extending through the housing (55) to define an annular recess therebetween for slidably receiving an upper tubular portion of a corresponding inlet port (32), as shown in FIG. 2C. In that regard, an internal cylindrical sidewall of the housing (55) of each of the caps (50) may be provided with one or a plurality of annular rings that project inward for slidable and sealing engagement with an outer sidewall surface of a corresponding inlet port (32).

Further, as shown in FIGS. 3A and 3B, the engagement member (56) may include a second end portion (56*b*) extending beyond the housing (55) for sliding engagement with a corresponding valve member (40) within a tubular top end portion (42) thereof. More particularly, a drive member (44) (e.g. one or more inward projecting rib) may be provided within the tubular top end portion (42). In turn, the second end portion (56*b*) of the engagement member (56) may define a complimentary mating member (e.g. one or more axial slot extending partially across the second end portion (56*b*) for receiving the drive member (44) therein) for abutting engagement with and driven rotation by the drive member (44) upon driven rotation of the valve member (40), e.g. by a corresponding valve actuator (3) comprising the compounder (2) referenced above.

In the later regard, and as shown in FIG. 3B, the valve member (40) may further comprise a bottom end portion (46) comprising a slot (46*a*) for receiving a top end of a corresponding valve actuator (3) of the compounder (2) referenced above. In turn, upon rotation of the given valve actuator (3), the corresponding valve member (40) may be co-rotated therewith, whereupon the corresponding cap (50) located on the corresponding inlet port (32) may be co-rotated from the locked position to the unlocked position relative to the corresponding inlet port (52).

In alternate embodiments, the caps (50) and the valve members (40) may have different complimentary drive member/mating member configurations to provide for co-rotation and sliding, axial engagement and disengagement. For example, the second end portion (56*b*) of caps (50) may comprise an x-shaped end or recess, and a bottom floor of the tubular top end portion (44) of the valve members (40) may comprise a complimentary, x-shaped recess or upstanding post, respectively.

With further reference to FIG. 3B, the valve member (40) may include at least one bottom peripheral ring (48*a*) extending outward about the entirety of the valve member (40) for sliding and sealing engagement with an inside surface of the lower tubular portion of a corresponding inlet port (32). Further the valve member (40) may include at least one top peripheral ring (48*b*) extending outward about the entirety of the valve member (40) for sliding and sealing engagement with the inside surface of the lower tubular portion of a corresponding inlet port (32), wherein the aforementioned hole (47) of the valve member is located between the at least one bottom peripheral ring (48*a*) and the at least one top peripheral ring (48*b*) thereof.

Returning now to FIG. 3A, the housing (55) of each cap (50) may include a locking element (58) for locking the cap (50) relative to the manifold (20) in the locked position, i.e. with the locking element (58) disposed under the locking plate (60). In the illustrated embodiment, the locking element (58) may comprise at least one peripheral protrusion extending outward from housing (55).

Reference is now made to FIGS. 4A and 4B which illustrate the locking plate (60) of the manifold (30). As described above and illustrated in FIGS. 4A and 4B, the locking plate (60) may comprise a plurality of apertures (62) for receiving the caps (50) therethrough. More particularly, each of the apertures (62) may be configured so that the locking plate (60) restricts axial movement of the locking element (58) of the caps (50) when located on the inlet ports (32) with the corresponding valve member (40) located in a corresponding first predetermined position. As shown, the peripheral edge of each of the apertures (62) may comprise a recess (65), sized to permit passage of the locking element (58) of a corresponding cap (50) therethrough in an unlocked position when the corresponding valve member is located in the corresponding predetermined second position.

Reference is now made to FIGS. 2A, 5A, 5B and 5C which illustrate compounding set-up features relating to the disposable apparatus (20). FIG. 2A illustrates the disposable apparatus (20) in an initial configuration for interconnection to the compounder (2) referenced above, with valve members (40) (not shown in FIG. 2A) oriented to receive corresponding ones of the valve actuators (3) referenced above. In the initial configuration, each of the caps (50) may be in the locked position with each of the caps disposed in a common first orientation (e.g. with opposing side portions (54*a*) oriented in parallel relation to a center axis AA of the manifold (30)).

Figure 5A:
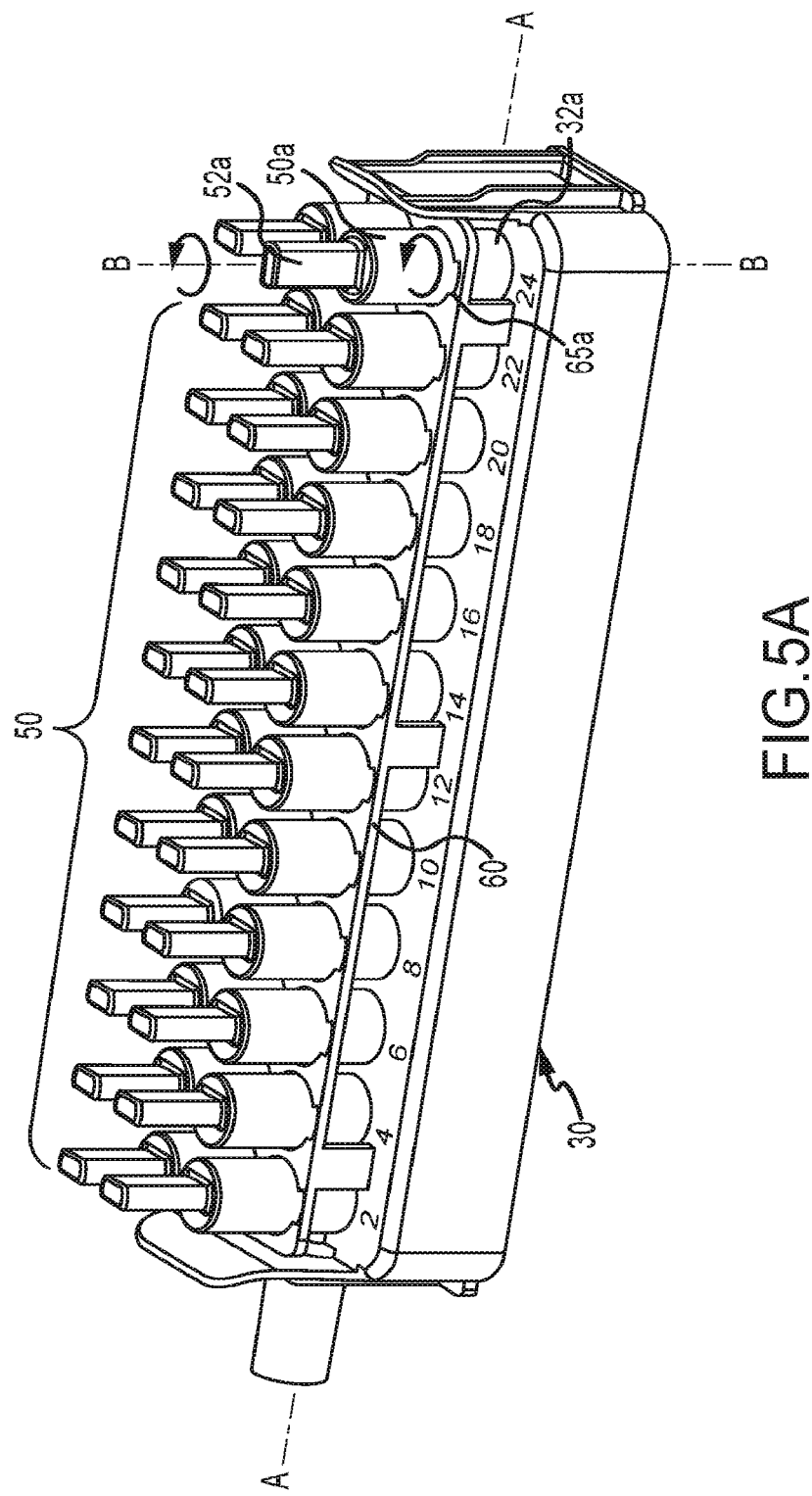
FIG. 5A is front perspective view of the disposable apparatus embodiment shown in FIGS. 2A-2C with one of the caps rotated from a locked position to an unlocked position.

In FIG. 5A, one of the caps (50*a*) has been rotated from the locked position to the unlocked position, relative to a predetermined one of the inlet ports (32*a*), by rotation of the corresponding valve member (40) from the corresponding first predetermined position to the corresponding second predetermined position. As shown, the remaining caps (50) remain in the locked position. In the locked position, the remaining caps (50) are restricted from removal from the corresponding inlet ports (32) by the locking plate (60).

In rotating to the unlocked position, cap (50*a*) has moved to a second orientation (e.g. with opposing side portions (54*a*) oriented in transverse relation to a center axis AA of the manifold (30)). By virtue of the asymmetric configuration of the top end portion (54), the unlocked cap (50a) may be readily differentiated from the remaining caps (50) by a user.

Figure 5B:
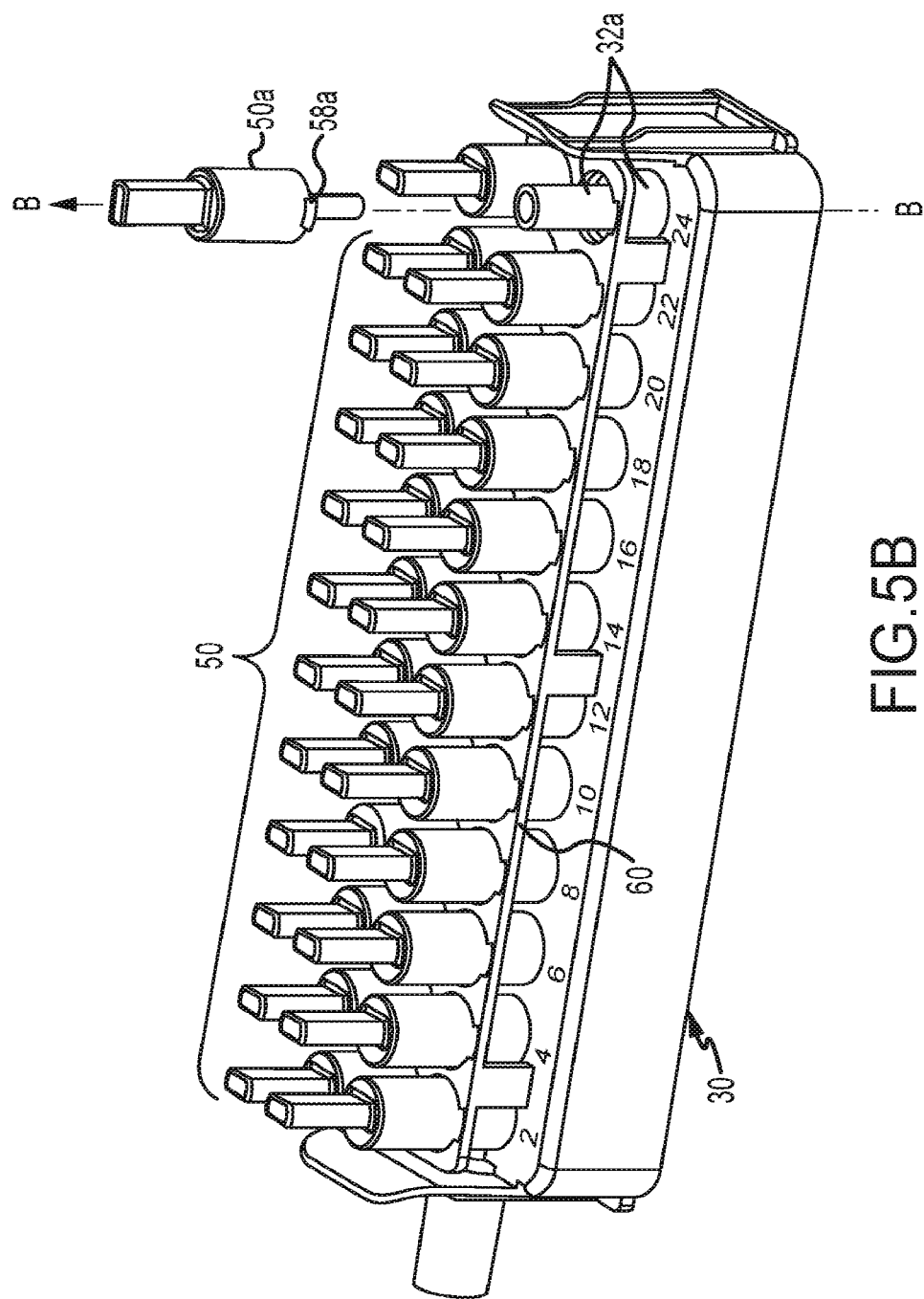
FIG. 5B is a front perspective view of the disposable apparatus embodiment shown in FIGS. 2A-2C, with the unlocked cap shown in FIG. 5A removed from a corresponding inlet port.

In the unlocked position, the locking element (58) (not shown in FIG. 2A) of the cap (50a) is aligned with the corresponding recess (65a) of the corresponding aperture (62a) of the locking plate (50a). Then, and as shown in FIG. 5B, the cap (50a) may be removed from the corresponding inlet port (32a) and disengaged from the corresponding valve member (40) (not shown in FIG. 2A) of the manifold (30) by sliding axial retraction.

Figure 5C:
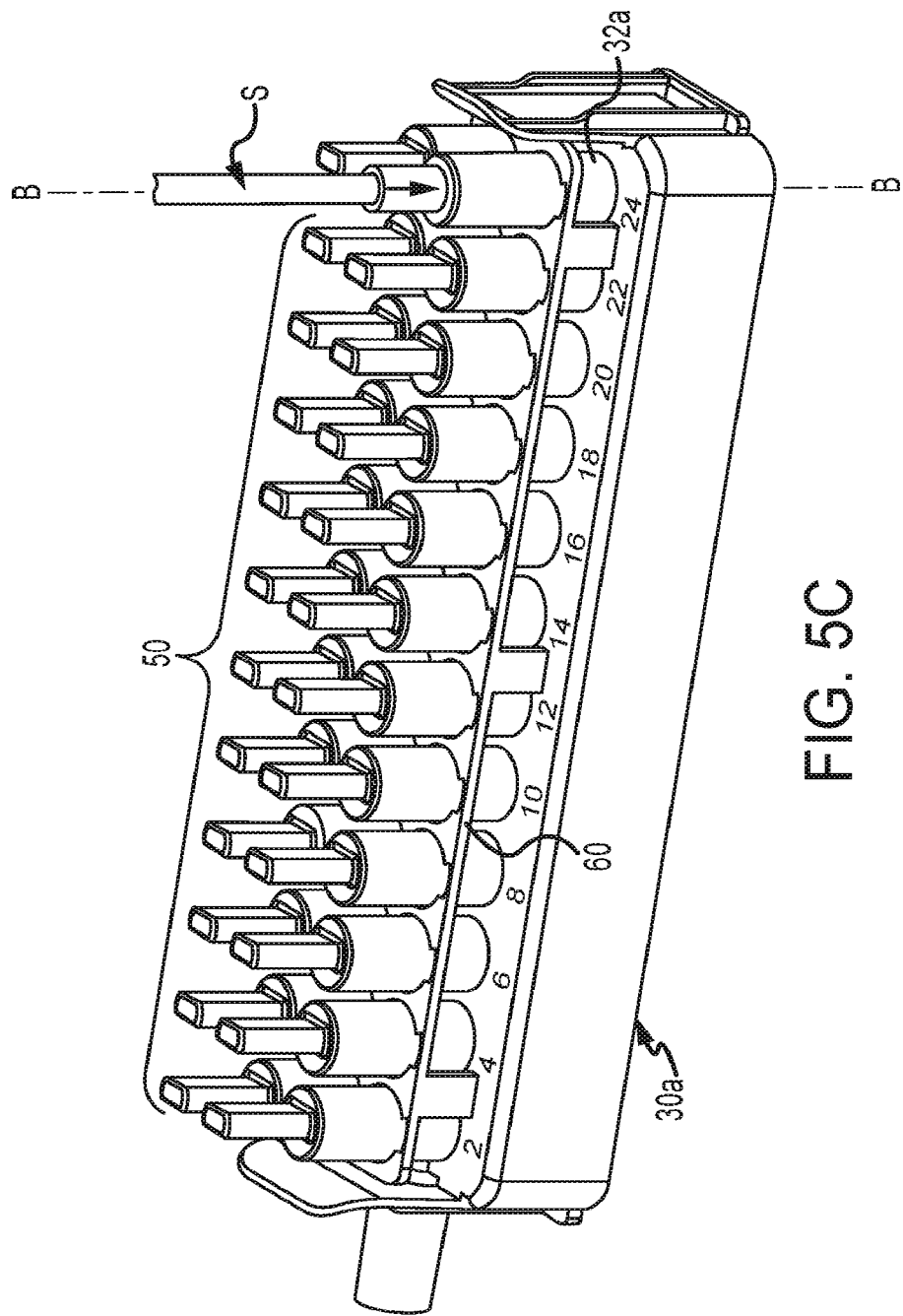
FIG. 5C is front perspective view of the disposable apparatus embodiment shown in FIGS. 2A-2C, with an end of a tubing set interconnected to the exposed inlet port shown in FIG. 5B.

In turn, and as illustrated in FIG. 5C, an end port of a predetermined tubing set S may be interconnected to the exposed inlet port (32a) of the manifold (30), wherein the predetermined tubing set S may be fluidly interconnected or interconnectable to a predetermined source container C containing a known fluid ingredient. Thereafter, successive ones of the remaining caps (50) may be rotated from the locked position to the unlocked position, relative to corresponding predetermined ones of the inlet ports (32), for successive interconnection of additional predetermined tubing sets S and predetermined source containers C, e.g. in accordance with a predetermined interconnection sequence as further discussed below.

In contemplated embodiments, the controller of the compounder (2) may be provided to control the movement of each of the valve actuators (3) in accordance with preprogrammed instructions comprising one or more stored software modules utilizing data stored in one or more databases at compounder (2). For example, the controller may be provided to separately control movement of each of the valve actuators (3) so as to separately move each of the valve members (40) between at least a corresponding first predetermined position, a corresponding second predetermined position and a corresponding third predetermined position. More particularly, the corresponding first predetermined position may be a "home position" in which a corresponding cap (50) may be located in a locked position with the corresponding fluid passageway from the corresponding inlet port (32) to the internal passageway (36) closed by the corresponding valve member (40). The corresponding second predetermined position may be a position in which the corresponding cap (50) may be in an unlocked position for manual removal from the corresponding inlet port (32). In contemplated embodiments, the valve member (40) may be provided to close the corresponding fluid passageway when located in the both the corresponding first predetermined position and the corresponding second predetermined position. The third predetermined position may be a position at which the valve member (40) is positioned so as to open the corresponding fluid passageway to permit fluid flow therethrough.

In one embodiment, the controller of the compounder (2) may be provided (e.g. preprogrammed) to control movement of the actuators (3) and correspondingly position each of the valve members (40) from a corresponding first predetermined position to a corresponding second predetermined position, and thereby move each of the corresponding caps (50) from the locked position to the unlocked position, in a predetermined interconnection sequence for set-up. In turn, predetermined ones of the plurality of inlet ports (32) may be provided for corresponding cap removal, and for attendant interconnection to different predetermined ones of a plurality of tubing sets S that are each interconnected or interconnectable to different predetermined ones of a plurality of source containers C (e.g. containing different fluid ingredients), in accordance with the predetermined interconnection sequence. The plurality of source containers C may be predetermined in relation to one or a plurality of predetermined formulations to be compounded pursuant to a given set-up procedure.

In one embodiment, the controller of the compounder (2) may be provided (e.g. preprogrammed) to require, between and for completion of successive steps in the predetermined interconnection sequence, the receipt and validation of an input at the controller. Such required input may be indicative of a desired interconnection between a corresponding predetermined one of the plurality of inlet ports (32) and a corresponding predetermined one of the plurality of the source containers C utilizing a corresponding predetermined one of the tubing sets S.

In that regard, the required input may include digital identifying data read from one or more machine readable marking(s) (e.g. a machine readable marking on a label attached to the corresponding predetermined source container and/or on a label attached to the predetermined corresponding tubing set S), utilizing the reader (6) described above in relation to FIG. 1B. In turn, the controller may be provided to compare the digital identifying data to stored data corresponding with the corresponding predetermined source container and/or corresponding with the corresponding predetermined tubing set S.

Upon receipt and validation of the required input for a given step in the predetermined interconnection sequence, additional ones of the valve members (40) may be successively positioned by corresponding valve actuators (3), under the control of the controller of compounder (2), between corresponding first and second predetermined positions for corresponding positioning of caps (50) between locked and unlocked positions (e.g. for corresponding cap removal) relative to predetermined successive ones of the inlet ports (32), and for interconnection of corresponding predetermined tubing sets S and corresponding predetermined source containers C to each of the corresponding inlet ports (32), in accordance with the predetermined interconnection sequence. Again, between and for completion of each successive step in the predetermined interconnection sequence, the receipt and validation of an input at the controller may be required, wherein the required input may be indicative of a desired interconnection between the corresponding predetermined one of the plurality of inlet ports (32) and the corresponding predetermined one of the plurality of the source containers C utilizing the corresponding predetermined one of the tubing sets S.

In one embodiment, after interconnection of each of the inlet ports (32) with the corresponding predetermined source container C utilizing the corresponding predetermined tubing set S, the controller may be operable (e.g. preprogrammed) to successively move the valve actuators (3) and thereby successively position the corresponding valve members (40) in the corresponding third predetermined position, in accordance with a predetermined priming sequence. Between each successive positioning step of the predetermined priming sequence, the pump P, described above in relation to FIG. 1B, may be operated under the control of the controller so as to draw the fluid ingredient from the corresponding predetermined container and thereby prime the corresponding predetermined inlet tubing set S, and corresponding inlet port (32), corresponding fluid passageway, internal passageway (36), and outlet port (38) of the manifold (30) (e.g. with any waste being collected in a waste bag connected to the outlet tubing OT). Further, between each successive positioning step of the predetermined priming sequence, and after a given corresponding priming operation, the controller may be operable to move the corresponding valve actuator (3) to thereby position the corresponding valve member (40) in a position to close the corresponding third passageway (e.g. the corresponding first or second predetermined position).

In one embodiment, after sequential interconnection of each of the predetermined inlet ports (32) with corresponding predetermined different ones of the source container(s) using corresponding predetermined different ones of the tubing sets S according to the predetermined interconnection sequence, and sequential priming of each of the inlet ports (32) and corresponding tubing sets S and attendant closure of each of the corresponding fluid passageways, in accordance with the predetermined priming sequence, the corresponding set-up procedure may be considered complete. In turn, the compounder (2) and disposable apparatus (20) may be utilized to compound one or a plurality of predetermined formulations.

In that regard, each predetermined formulation may be provided to the compounder (2) in electronic form. By way of example, the compounder (2) may be provided to receive or otherwise obtain (e.g. from a network) an electronic file comprising one more predetermined formulation orders, wherein each of the formulation orders identify the ingredients and the amounts of each different ingredient to be included in the given formulation.

Thereafter, for each given formulation, the controller of the compounder (2) may be operable (e.g. preprogrammed) to successively control different ones of the valve actuators (3) so as to successively position corresponding ones of the valve members (40) in the corresponding predetermined third position (e.g. so as to open corresponding fluid passageway) and thereafter in another corresponding predetermined position (e.g. so as to close the corresponding fluid passageway), in successive steps of a predetermined formulation sequence. As may be appreciated, when each given valve member (40) is positioned in the corresponding third predetermined position, the controller may control operation of the pump P so as to flow a predetermined amount of the corresponding fluid ingredient from the corresponding source container C through the corresponding inlet port (32) for compounding into the given predetermined formulation in a receiving receptacle R.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only preferred embodiment and variants thereof have been shown and described and that all changes and modifications that come within the spirit of the invention are desired to be protected.

What is claimed:

1. A system, comprising:
  a multi-ingredient compounder having a plurality of valve actuators and a controller for controlling movement of each of the plurality of valve actuators; and,
  a disposable apparatus including:
    a manifold having a plurality of inlet ports;
    a plurality of valve members, each locatable to interface with a different corresponding one of said plurality of valve actuators for driven movement thereby between a plurality of different positions relative to a different corresponding one of said plurality of inlet ports; and
    a plurality of caps located on different corresponding ones of the plurality of inlet ports, wherein the controller is operable to separately control movement of each of the plurality of actuators so as to separately move each of the plurality of valve members between at least a corresponding first predetermined position at which the corresponding cap is locked relative to the manifold and a corresponding second predetermined position at which the corresponding cap is unlocked relative to the manifold.

2. The system of claim 1, wherein each of the plurality of caps is engageable with the corresponding valve member for co-movement therewith, from a locked position to an unlocked position, when the corresponding valve member is moved from the corresponding first predetermined position to the corresponding second predetermined position.

3. The system of claim 2, wherein each of the plurality of valve members is disposed for rotatable movement between the corresponding first predetermined position and the corresponding second predetermined position, wherein the corresponding cap is co-rotatable from the locked position to the unlocked position.

4. The system of claim 3, wherein each of the plurality of caps is slidably disposed on the corresponding inlet port for rotation on and relative to the inlet port during rotation from the locked position to the unlocked position.

5. The system of claim 2, wherein the controller is operable to control movement of said plurality of valve actuators to correspondingly position each of said plurality of valve members separately from the corresponding first predetermined position to the corresponding second predetermined position in a predetermined interconnection sequence, wherein the corresponding caps are separately positioned from the locked position to the unlocked position in accordance with the predetermined sequence, and wherein predetermined ones of the corresponding inlet ports are successively accessible for interconnection to different predetermined ones of a plurality of tubing sets and different corresponding ones of a plurality of source containers in accordance with the predetermined interconnection sequence.

6. The system of claim 5, wherein said controller is operable to require, between and for completion of successive steps in said predetermined interconnection sequence, controller receipt and validation of an input indicative of a desired interconnection between a corresponding predetermined one of the plurality of inlet ports and a corresponding predetermined one of said plurality of source containers utilizing a corresponding predetermined one of said plurality of tubing sets.

7. The system of claim 6, wherein said required input comprises digital identifying data read from at least one machine readable marking located on at least one of the corresponding predetermined one of the plurality of source containers and the corresponding predetermined one of said plurality of tubing sets.

8. The system of claim 7, wherein said controller is operable to compare the digital identifying data to stored data corresponding with at least one of said corresponding predetermined one of said plurality of source containers and said corresponding predetermined one of said tubing sets.

9. The system of claim 8, wherein after completion of said predetermined interconnection sequence, said controller is operable to separately control movement of each of the plurality of actuators so as to separately move each of the plurality of valve members, in a predetermined priming sequence, between the corresponding second predetermined corresponding position and a predetermined third position to open the corresponding fluid passageway for priming, and between the corresponding third predetermined position to another corresponding predetermined position to close the corresponding fluid passageway.

10. A system, comprising:
a manifold having an internal passageway, an outlet port located at one end of the internal passageway, and a plurality of inlet ports to the internal passageway;
a plurality of valve members, each disposed for movement relative to a different corresponding one of the plurality of inlet ports to open and close a corresponding fluid passageway between the corresponding inlet port and internal passageway of the manifold;
a plurality of caps, each locatable on a different corresponding one of said plurality of inlet ports and engageable with the corresponding valve member; and
a controller, operable to control movement of the plurality of valve members from a corresponding first predetermined position to a corresponding second predetermined position,
wherein each of said plurality of caps is engageable with the corresponding valve member for co-movement therewith and relative to the corresponding inlet port when the corresponding valve member is moved from the corresponding first predetermined position to the corresponding second predetermined position.

11. The system of claim 10, wherein each of said plurality of caps is restricted from removal from the corresponding inlet port in a locked position when the corresponding valve member is located in the corresponding first predetermined position relative to the corresponding inlet port, and is removable from the corresponding inlet port in an unlocked position when the corresponding valve member is moved to the corresponding second predetermined position relative to the corresponding inlet port, and wherein each of said plurality of valve members is disposed for rotatable movement between said corresponding predetermined first position and said corresponding predetermined second position, and wherein the corresponding cap is co-rotatable from the locked position to the unlocked position.

12. The system of claim 11, wherein the controller is operable to control movement of said plurality of valve members to correspondingly position each of said plurality of valve members separately from the corresponding first predetermined position to the corresponding second predetermined position in a predetermined interconnection sequence, wherein the corresponding caps are separately positioned from the locked position to the unlocked position in accordance with the predetermined sequence, and wherein predetermined ones of the corresponding inlet ports are successively accessible for interconnection to different predetermined ones of a plurality of tubing sets and different corresponding ones of a plurality of source containers in accordance with the predetermined interconnection sequence.

13. The system of claim 11, wherein each of said plurality of caps is slidably removable in the unlocked position from the corresponding inlet port upon axial movement relative to the corresponding inlet port.

14. The system of claim 13, wherein each of said plurality of valve members comprises a drive member and each of the corresponding caps comprises a complimentary mating member for abutting engagement with and driven rotational movement by the drive member of the corresponding valve member, and wherein each of said plurality of caps is slidably disengageable in the unlocked position from the drive member of the corresponding valve member upon said axial movement relative to the corresponding inlet port.

15. The system of claim 11, wherein each of said plurality of caps comprises at least one locking element, and wherein said manifold further comprises:
a plurality of apertures, wherein each of said plurality of caps extends through a different corresponding one of said plurality of apertures when located on said corresponding inlet port, and wherein each said plurality of apertures is configured so that said manifold restricts axial movement of the locking element of the corresponding cap when located on the corresponding inlet port with the corresponding valve member located in said corresponding first predetermined position relative to the corresponding inlet port.

16. The system of claim 15, wherein said at least one locking element of each of said plurality of caps comprises:
at least one peripheral protrusion.

17. The system of claim 16, wherein each of said plurality of apertures each include at least one edge recess configured so that said manifold permits axial movement of the at least one peripheral protrusion of the corresponding cap through said at least one edge recess when the corresponding valve member is located in said corresponding second predetermined position relative to the corresponding inlet port.

18. The system of claim 15, wherein said manifold further includes:
a base portion defining said internal passageway, outlet port, and plurality of inlet ports; and
a locking plate defining said plurality of apertures, wherein said locking plate is selectively interconnectable to said base portion.

19. The system of claim 18, wherein the at least one locking element of each of said plurality of caps is located between said base portion and said locking plate when the corresponding valve member is located in the corresponding first predetermined position.

* * * * *